United States Patent [19]

Ritschel et al.

[11] Patent Number: 4,482,724

[45] Date of Patent: Nov. 13, 1984

[54] BISIMIDAZOLINES

[75] Inventors: Werner Ritschel, Hofheim am Taunus; Helmut Diery, Kelkheim; Martin Hille, Liederbach, all of Fed. Rep. of Germany

[73] Assignee: Hoechst Aktiengesellschaft, Fed. Rep. of Germany

[21] Appl. No.: 411,521

[22] Filed: Aug. 25, 1982

[51] Int. Cl.³ .................. C07D 233/18; C07D 233/14; C07D 233/16

[52] U.S. Cl. .................................................. 548/350

[58] Field of Search ........................................ 548/350

[56] References Cited

U.S. PATENT DOCUMENTS

| | | | |
|---|---|---|---|
| 2,646,399 | 7/1953 | Hughes | 548/350 X |
| 2,647,125 | 7/1953 | Gunderson | 548/350 X |
| 2,940,927 | 6/1960 | Hughes | 548/350 X |
| 3,017,352 | 1/1962 | Hughes et al. | 548/350 X |

OTHER PUBLICATIONS

Goebel, C., J. Am. Oil Chem. Soc., 24, 65-68 (1947).

Primary Examiner—Richard A. Schwartz
Attorney, Agent, or Firm—Connolly & Hutz

[57] ABSTRACT

New bisimidazolines of the formula

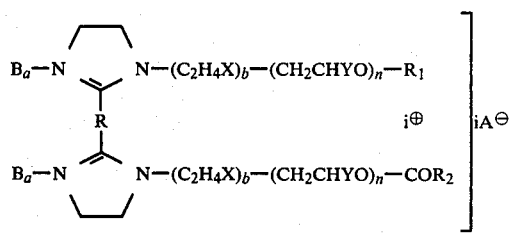

wherein

R denotes the alkyl skeleton of a dimerised fatty acid having 22 to 42, preferably 34, C atoms, X denotes an oxygen atom or a group of the formula $\supset N-B_m$, B denotes hydrogen, methyl, ethyl, benzyl or a group of the formula $-(CH_2CHYO)_n-R_1$, Y denotes hydrogen, methyl or ethyl, $R_1$ denotes hydrogen or a group $-COR_2$, $R_2$ denotes $C_1$-$C_{22}$, preferably $C_8$-$C_{22}$, alkyl, a denotes 0 or 1, b denotes a number from 0 to 4, m denotes 1 or 2, n denotes a number from 0 to 100, preferably 0 to 20, i denotes a number from 0 to 2b+2 and A denotes an anion.

A process for their preparation and their use a demulsifiers for crude petroleum emulsions.

3 Claims, No Drawings

BISIMIDAZOLINES

It is known that, during the lifting of crude oil emulsions, there is an increase in the water content of the crude oils lifted. This water, which is also lifted, forms a water-in-oil emulsion with the crude oil, it being possible for salts, such as sodium chloride, calcium chloride and magnesium chloride, to be dissolved in the water present in the emulsion. In addition, carbon dioxide and hydrogen sulfide are frequently present in the crude oil emulsions. All these substances produce corrosion damage in the lifting equipment and in the refinery, so that it is necessary, for this reason alone, to remove the salt-containing water from the crude oil emulsion with the aid of demulsifiers.

A demulsifier has the purpose of breaking the emulsion at a concentration used which is as low as possible and of bringing about in this separation process a complete separation out of water and a reduction of the salt content to a minimum, as far as possible without expenditure or with a minimum amount of additional heat. The criteria for the quality of delivered crude oil are the residual content of salt and the water content.

Crude oils have different compositions depending on their origin, and the natural emulsion stabilizers present in the oil have a complicated and variable chemical composition, so that specific demulsifying agents must be developed for each oil. The requirements placed on a demulsifier become even greater due to the varying conditions of lifting and processing. Due to the continuous opening up of new oil fields and change in the lifting conditions of old oil fields, the development of optimum demulsifiers for each particular purpose thus remains a pressing need.

Reaction products of alkylene oxide with alkylphenol-aldehyde resins are already known as non-ionic demulsifiers for crude petroleum emulsions (U.S. Pat. Nos. 2,499,368, 2,499,370, 2,560,333 and 2,574,543). The use of block polymers and copolymers of propylene oxide and ethylene oxide for this purpose is also known (French Pat. No. 1,069,615 and German Auslegeschrift No. 1,018,179).

It has now been found that new bisimidazolines not only exhibit an excellent activity as demulsifiers for crude oil, but also good effects as corrosion inhibitors.

The invention relates to new bisimidazolines of the formula $$\left[ \begin{array}{c} B_a-N \diagdown \diagup N-(C_2H_4X)_b-(CH_2CHYO)_n-R_1 \\ \phantom{B_a-N}R \\ B_a-N \diagup \diagdown N-(C_2H_4X)_b-(CH_2CHYO)_n-COR_2 \end{array} \right]^{i\oplus} iA^{\ominus}$$

wherein

R denotes the alkyl skeleton of a dimerized fatty acid having 22 to 42, preferably 34, C atoms, X denotes an oxygen atom or a group of the formula $>N-B_m$, B denotes hydrogen, methyl, ethyl, benzyl or a group of the formula $-(CH_2CHYO)_n-R_1$, Y denotes hydrogen, methyl or ethyl, $R_1$ denotes hydrogen or a group $-COR_2$, $R_2$ denotes $C_1-C_{22}$, preferably $C_8-C_{22}$, alkyl, a denotes 0 or 1, b denotes a number from 0 to 4, m denotes 1 or 2, n denotes a number from 0 to 100, preferably 0 to 20, i denotes a number from 0 to 2b+2 and A denotes an anion such as, for example, the chloride, bromide, methyl sulfate, ethyl sulfate or dialkyl phosphate ion. The symbols X, B, Y, $R_1$, $R_2$, a, b, m and n listed above can each have meanings within one compound which are identical or different from one another.

Preparation of the compounds of the above formula is carried out by initially condensing a dimerized fatty acid of the formula II $$HOOC-R-COOH \qquad (II)$$

with a diamine or polyamine of the formula III $$H_2N-CH_2CH_2-NH-(CH_2CH_2X)_bH \qquad (III)$$

to give a bisimidazoline of the formula IV $$\begin{array}{c} N \diagdown \diagup N-(C_2H_4X)_bH \\ R \\ N \diagup \diagdown N-(C_2H_4X)_bH, \end{array} \qquad (IV)$$

reacting this bisimidazoline of the formula IV, if appropriate, with ethylene oxide and/or propylene oxide or butylene oxide, esterifying the reaction product obtained with an acid of the formula V $$HOOC-R_2 \qquad (V)$$

and then, where appropriate, quaternizing or neutralizing.

The preferred products suitable as dimerized fatty acids are those commercially available under the names ®Pripol 1010, ®Pripol 1022 and Fatty Acid 7002. These products can also contain proportions of trimeric or more highly condensed fatty acids. Thus, for example, Pripol 1022 contains about 20% of trimeric constituents and Pripol 1010 only contains about 3% of these. These dimerized fatty acids are initially condensed with two moles of a diamine or polyamine of the formula III. Examples of amines of this type are aminoethylethanolamine, ethylenediamine, diethylenetriamine, triethylenetetramine or pentaethylenehexamine. The condensation can be carried out without solvent in a melt of the reactants or in the presence of an inert solvent at the boiling point of the solvent. The preferred solvent for this purpose is toluene or xylene, which simultaneously serves to remove the water formed in the reaction.

The bisimidazoline of the formula IV produced by this condensation can then, depending on the value selected for the symbol n, be oxalkylated by known methods, preferably in the presence of a basic catalyst, such as sodium methylate or sodium hydroxide. Suitable alkylene oxides are, preferably, ethylene oxide, and also mixtures of ethylene oxide with propylene oxide or butylene oxide.

These oxalkylation products or, when n is 0, the bisimidazolines of the formula IV are then esterified with one or more carboxylic acids of the formula V. $C_8$–$C_{22}$ fatty acids are preferably employed as carboxylic acids. The ratio of the amounts of carboxylic acids and bisimidazoline of the formula IV, or its oxalkylation products, can be selected such that one or more acyl groups are present in the ester.

The esterification can be carried out with pure carboxylic acids of the formula V or with mixtures of various carboxylic acids of this type. In analogy to the first step, the reaction in this case can also be carried out in the melt of the reactants at temperatures of about 160°–180° C. or in an inert solvent as described above.

The esters thus obtained can then be quaternized, either by simple addition of acids, such as, for example, acetic acid, sulfuric acid or phosphoric acid, for the case when B is H, or by reaction with alkylating reagents such as, for example, methyl chloride, benzyl chloride, dimethyl sulfate or trimethyl phosphate, preferably at temperatures of 60°–70° C. in a lower alcohol or in toluene.

The products thus obtained are very suitable, both in their quaternized and also in their partially quaternized or non-quaternized or neutralized form, for the demulsification of crude oil emulsions. These products are added to the crude oil emulsion in concentrations of 2 to 400, preferably 5 to 50, ppm, either in an undiluted form or as solutions which have been diluted with an organic solvent in a ratio of up to 1:200.

The following Examples are intended to illustrate the invention.

GENERAL PROCEDURE FOR THE PREPARATION OF THE BISIMIDAZOLINES IV a–c FOR THE EXAMPLES 1–7

0.5 mole of a dimeric fatty acid is heated with 1 mole of an amine in 300 g of xylene under a water separator until about 36 ml of water have circulated out. After removal of the xylene by distillation, the product obtained is viscous, but still pourable. Preparation of IVa: by the general procedure from 285 g (0.5 mole) of the dimeric fatty acid "Pripol 1022" and 103 g (1 mole) of diethylenetriamine. Preparation of IVb: from 285 g (0.5 mole) of "Pripol 1022" and 104 g (1 mole) of aminoethylethanolamine. Preparation of IVc: from 285 g (0.5 mole) of "Pripol 1010" and 103 g (1 mole) of diethylenetriamine. The bisimidazolines IVa–IVc show the characteristic C=N absorption at 1610 cm$^{-1}$ in the IR spectrum.

EXAMPLE 1

250 g (1 mole) of stearic acid were added to the solution of the bisimidazoline IVa, prepared according to the general procedure, in 300 g of xylene and the mixture was heated further until 18 ml of $H_2O$ had circulated out. After removal of the xylene by distillation, 650 g of isobutanol were added and quaternization with methyl chloride was carried out in an autoclave at 70° C. A brown pourable fluid was obtained, having a content of 50% of the compound of the formula

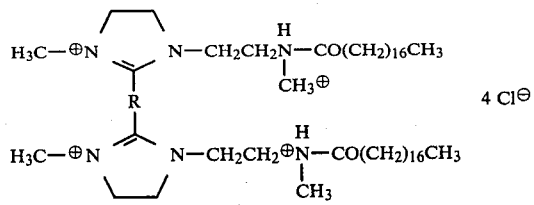

In this formula, as also in those below, R denotes the $C_{34}$ alkyl skeleton of a dimerized fatty acid.

EXAMPLE 2

After reaction of the bisimidazoline IVa with 250 g of stearic acid as in Example 1, 60 g (1 mole) of glacial acetic acid were stirred in at 60° C. After removal of the xylene by distillation and addition of 650 g of isobutanol, a solution was obtained having a content of 50% of the compound of the formula

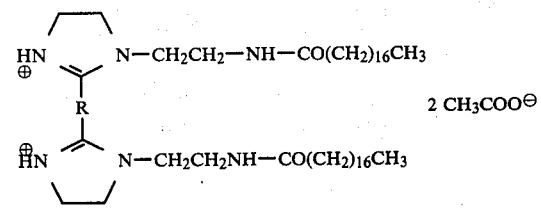

EXAMPLE 3

125 g (0.5 mole) of stearic acid were added to a solution of the imidazoline IVb in 300 g of xylene and 9 ml of $H_2O$ were azeotroped out in a water separator. After removal of the xylene by distillation, 520 g of isobutanol were added and reaction with methyl chloride in an autoclave at 70° C. was continued until no further absorption occurred. A 50% strength solution in isobutanol of the compund of the formula

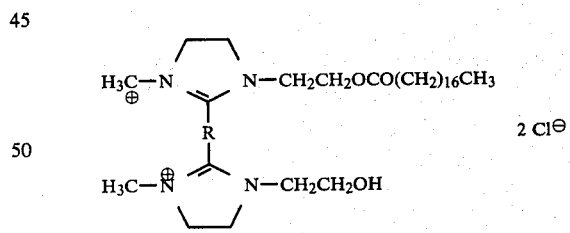

was obtained.

EXAMPLE 4

220 g (5 moles) of ethylene oxide were added onto the bisimidazoline IVb in an autoclave, after the addition of 1.5 g of powdered NaOH, at 160° C. and 5 bar. Then 125 g (0.5 mole) of stearic acid were added and the mixture was heated in a distillation apparatus at 160°–180° C., until 9 ml of water had been distilled off. After adding 730 g of isobutanol, quaternization with methyl chloride was carried out in an autoclave at 70° C. A 50% strength solution in isobutanol of the compound of the formula

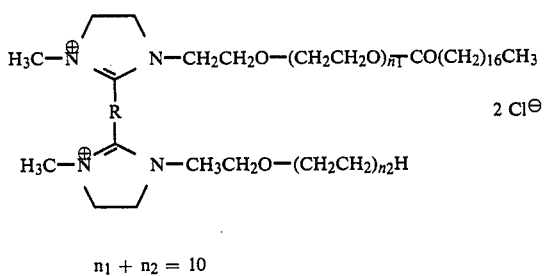

$n_1 + n_2 = 10$ was obtained.

EXAMPLE 5

660 g (15 moles) of ethylene oxide were added onto the bisimidazoline IVb in an autoclave in a known manner. Then 250 g (1 mole) of stearic acid were added and 18 ml of H$_2$O were distilled off in a distillation apparatus. After the addition of 1,300 g of isobutanol, quaternization was carried out with methyl chloride. The solution produced contained 50% of the compound of the formula

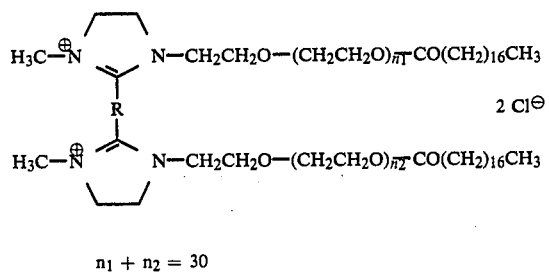

$n_1 + n_2 = 30$

EXAMPLE 6

Initially, 220 g (5 moles) of ethylene oxide and then 280 g (5 moles) of propylene oxide were added onto the bisimidazoline IVc by the customary method. Then 380 g (1.5 moles) of tallow fatty acid were added and the mixture was heated in a distillation apparatus until 27 ml of H$_2$O had distilled off. 1,200 g of isobutanol were added and a brown, pourable liquid was obtained, which contained 50% of the active substance of the following formula

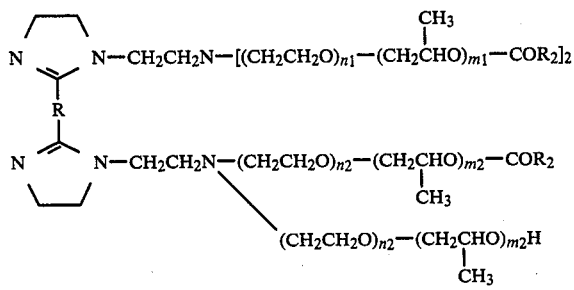

$R_2$ = tallow fatty alkyl, $2(n_1 + n_2) = 10$, $2(m_1 + m_2) = 10$

EXAMPLE 7

110 g (2.5 moles) of ethylene oxide were added onto the bisimidazoline IVa in a customary manner, and then esterification was carried out with 500 g (2 moles) of tallow fatty acid. After the addition of 925 g of isobutanol, a 50% strength solution of the compound of the formula

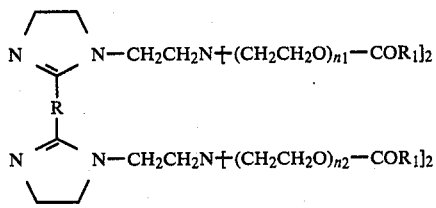

$R_1$ = tallow fatty alkyl, $n_1 + n_2 = 5$ was obtained.

EXAMPLE 8

420 g (0.5 mole) of the dimeric fatty acid "Fatty Acid 7002" were heated with 104 g (1 mole) of aminoethylethanolamine without solvent until 36 ml of H$_2$O had distilled off. Then 72 g (0.5 mole) of 2-ethylhexanoic acid were added and a further 9 ml of H$_2$O were distilled off. After adding 630 g of isobutanol, quaternization with 80 g of dimethyl sulfate was carried out at 65° C., a 50% strength solution (in isobutanol) of the compound of the following formula

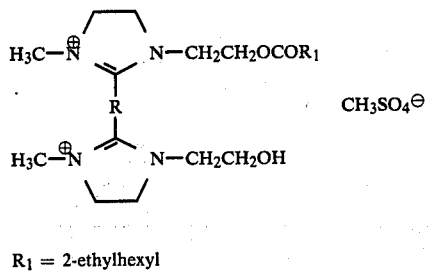

$R_1$ = 2-ethylhexyl being obtained.

In the Tables below, the demulsifying activity on crude oil emulsions of the compounds according to the invention under the conditions and with the amounts used, which are customary in the oil fields, are listed.

For this purpose, the demulsifiers were used in 50% strength isobutanolic solutions which were injected with micrometering devices. The separation out of the emulsified water was carried out in conical tubes which were calibrated and could be stoppered and the amount of the emulsion was 100 cm$^3$ in each case. The amounts of emulsion water which separated out in set times are reported in the Tables in %. The absolute water content of the emulsions was determined in preliminary experiments by the Dean-Stark method in each case. The amount of demulsifiers added, the absolute water content of the emulsion, the separating temperature and the origin of the emulsion are listed in the individual Tables.

TABLE I

| Demulsification temperature: | 50° C. |
| --- | --- |
| Water content of the emulsion: | 43% |
| Amount added: | 40 ppm |
| Origin: | North Sea |
| Data: | % separation of water |

| Compound from | Minutes | | | | | |
| --- | --- | --- | --- | --- | --- | --- |
| Example | 10 | 20 | 30 | 60 | 120 | 180 |
| 1 | 12 | 33 | 63 | 78 | 92 | 99 |
| 2 | 14 | 38 | 68 | 85 | 98 | 100 |
| 3 | 16 | 39 | 71 | 90 | 100 | 100 |
| 4 | 13 | 35 | 68 | 83 | 91 | 98 |
| 5 | 11 | 34 | 65 | 81 | 90 | 97 |
| 6 | 18 | 38 | 69 | 88 | 100 | 100 |
| 7 | 12 | 35 | 67 | 86 | 95 | 99 |
| 8 | 18 | 38 | 69 | 91 | 98 | 100 |
| no addition | 0 | 0 | 0 | 0 | 0 | 0 |

TABLE II

| Demulsification temperature: | 40° C. |
| --- | --- |
| Water content: | 65% |
| Amount added: | 50 ppm |
| Origin: | Emsland |
| Data: | % separation of water |

| Compound from | Minutes | | | | |
| --- | --- | --- | --- | --- | --- |
| Example | 10 | 30 | 60 | 120 | 180 |
| 1 | 12 | 33 | 62 | 78 | 93 |
| 2 | 21 | 54 | 88 | 96 | 100 |
| 3 | 25 | 62 | 93 | 100 | 100 |
| 4 | 17 | 48 | 74 | 98 | 100 |
| 5 | 16 | 38 | 74 | 92 | 98 |
| 6 | 24 | 54 | 83 | 98 | 100 |
| 7 | 20 | 48 | 83 | 94 | 100 |
| 8 | 22 | 43 | 76 | 91 | 97 |
| no addition | 0 | 0 | 0 | 0 | 0 |

TABLE III

| Demulsification temperature: | 52° C. |
| --- | --- |
| Water content: | 28% |
| Amount added: | 60 ppm |
| Origin: | Borneo |
| Data: | % separation of water (W), % interface (sludge) (I) |

| Compound from | Minutes | | | | | | | |
| --- | --- | --- | --- | --- | --- | --- | --- | --- |
| | 20 | | 60 | | 120 | | 180 | |
| Example | % W | % I | % W | % I | % W | % I | % W | % I |
| 1 | 40 | 15 | 85 | 4 | 93 | 1.0 | 98 | 1.0 |
| 2 | 36 | 18 | 78 | 6 | 90 | 3.5 | 96 | 2.0 |
| 3 | 42 | 15 | 85 | 3 | 98 | 1.0 | 100 | 0 |
| 4 | 42 | 11 | 85 | 2.5 | 98 | 0.5 | 100 | 0 |
| 5 | 51 | 10 | 90 | 1.0 | 100 | 0 | 100 | 0 |
| 6 | 47 | 12 | 88 | 2.0 | 99 | 0.2 | 100 | 0 |
| 7 | 53 | 8 | 88 | 1.5 | 100 | 0 | 100 | 0 |
| 8 | 40 | 14 | 79 | 5 | 94 | 1.5 | 98 | 1.5 |
| no addition | 0 | 100 | 0 | 100 | 0 | 100 | 0 | 100 |

TABLE IV

| Demulsification temperature: | 48° C. |
| --- | --- |
| Water content: | 19% |
| Amount added: | 50 ppm |
| Origin: | Nigeria |
| Data: | % separation of water (W), % interface related to oil (I) |

| Compound from | Minutes | | | | | | | |
| --- | --- | --- | --- | --- | --- | --- | --- | --- |
| | 30 | | 60 | | 120 | | 180 | |
| Example | % W | % I | % W | % I | % W | % I | % W | % I |
| 1 | 55 | 8.0 | 88 | 2.0 | 96 | 1.0 | 99 | 0.5 |
| 2 | 58 | 6.0 | 91 | 1.5 | 99 | 0.5 | 100 | 0 |
| 3 | 50 | 10.0 | 97 | 2.5 | 100 | 0 | 100 | 0 |
| 4 | 53 | 7.0 | 96 | 1.5 | 100 | 0 | 100 | 0 |
| 5 | 61 | 6.5 | 98 | 1.0 | 100 | 0 | 100 | 0 |
| 6 | 58 | 7.0 | 97 | 1.0 | 100 | 0 | 100 | 0 |
| 7 | 55 | 7.5 | 90 | 1.5 | 99 | 1.5 | 99 | 0.5 |
| 8 | 48 | 11.0 | 85 | 3.0 | 93 | 2.0 | 97 | 1.0 |
| no addition | 0 | 100 | 0 | 100 | 0 | 100 | 0 | 100 |

INHIBITION OF CORROSION

In order to find the activity as a corrosion inhibitor, test strips of carbon steel having a surface area of 20 $cm^2$ were immersed in 20% strength sodium chloride solutions at 60° C. for 6 hours in each case, the solutions containing an addition of 10 mg/l, 20 mg/l or 30 mg/l of the product to be tested. A continuous stream of carbon dioxide was bubbled through the test solutions during the test. The absolute loss in weight of the metal strips subsequently determined served as a measure of the corrosive effect.

The results obtained are compiled in Table V.

TABLE V

| Amount employed, mg/l | | | |
| --- | --- | --- | --- |
| Product according to Example | 10 | 20 | 30 |
| | Loss in weight, mg | | |
| 1 | 2.6 | 2.6 | 2.8 |
| 2 | 8.5 | 6.2 | 5.5 |
| 3 | 3.3 | 3.1 | 2.8 |
| 4 | 21.0 | 14.0 | 7.0 |
| 5 | 23.0 | 14.0 | 7.5 |
| 6 | 20.0 | 11.0 | 6.3 |
| 7 | 7.9 | 4.6 | 3.0 |
| 8 | 4.8 | 3.3 | 2.7 |
| no addition | — | 24.5 | — |

The results of the investigations show that the products used according to the invention have the characteristic properties of a good demulsifier and, at the same time, those of a corrosion inhibitor. They also show that the sludge associated with the crude oil emulsions from Borneo or Nigeria, which are difficult to demulsify, is reduced to a large extent on using these products.

We claim:

1. A bisimidazoline of the formula

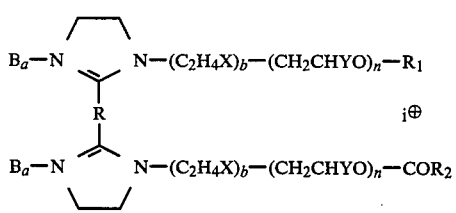

wherein

R denotes the alkyl skeleton of a dimerized fatty acid having 22 to 42 C atoms,

X denotes an oxygen atom or a group of the formula $\gtrsim N-B_m$,

B denotes hydrogen, methyl, ethyl, benzyl or a group of the formula $-(CH_2CHYO)_n-R_1$, Y denotes hydrogen, methyl or ethyl, $R_1$ denotes hydrogen or a group $-COR_2$, $R_2$ denotes $C_1-C_{22}$ alkyl, a denotes 0 or 1; b denotes a number up to 4 which is at least 1; m denotes 1 or 2, n denotes a number from 0 to 100, i denotes a number from 0 to 2b+2; and A denotes an anion.

2. A bisimidazoline according to claim 1, wherein said $R_2$ denotes $C_8-C_{22}$ alkyl; said b is 1; and said n denotes a number from 0 to 20.

3. A bisimidazoline according to claim 2 wherein said R denotes the alkyl skeleton of a dimerized fatty acid having 34 C atoms.

* * * * *